US010005270B2

(12) United States Patent
Rist et al.

(10) Patent No.: US 10,005,270 B2
(45) Date of Patent: Jun. 26, 2018

(54) VACUUM JIGS INCLUDING ULTRAVIOLET LIGHT SENSORS AND METHODS OF OPERATING THE SAME

(71) Applicant: Toyota Motor Engineering & Manufacturing North America, Inc., Erlanger, KY (US)

(72) Inventors: Donald E. Rist, Richmond, KY (US); Jacob T. Kendall, Georgetown, KY (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 170 days.

(21) Appl. No.: 15/231,913

(22) Filed: Aug. 9, 2016

(65) Prior Publication Data

US 2018/0043675 A1    Feb. 15, 2018

(51) Int. Cl.
*B32B 41/00* (2006.01)
*G01N 21/64* (2006.01)
*B32B 37/10* (2006.01)

(52) U.S. Cl.
CPC .......... *B32B 41/00* (2013.01); *B32B 37/1018* (2013.01); *G01N 21/64* (2013.01); *B32B 2307/422* (2013.01); *B32B 2605/00* (2013.01)

(58) Field of Classification Search
CPC . B32B 41/00; B32B 37/1018; B32B 2605/00; B32B 2307/422; G01N 21/64
USPC ........................... 156/64, 350, 351, 378, 379
See application file for complete search history.

(56) References Cited

U.S. PATENT DOCUMENTS

| 4,741,860 A | 5/1988 | Hartman |
| 7,216,461 B1* | 5/2007 | Clemmer ............. A47B 77/022 52/177 |
| 8,671,813 B2 | 3/2014 | Tannas |
| 2010/0098951 A1 | 4/2010 | Fassler et al. |

FOREIGN PATENT DOCUMENTS

| CN | 204194989 U | 3/2015 |
| CN | 104889498 A | 9/2015 |
| CN | 104260020 B | 3/2016 |
| JP | S60-7696 A | 1/1985 |

* cited by examiner

*Primary Examiner* — Michael N Orlando
*Assistant Examiner* — Joshel Rivera
(74) *Attorney, Agent, or Firm* — Dinsmore & Shohl LLP

(57) ABSTRACT

A method for operating a vacuum jig may include emitting an ultraviolet light from an ultraviolet light source; detecting, using an ultraviolet light sensor, luminescence of a coating on a surface responsive to emission of the ultraviolet light; determining whether the detected luminescence is greater than or equal to a predetermined threshold luminescence; and enabling a vacuum-assisted coupling of the vacuum jig when the detected luminescence is greater than or equal to the predetermined threshold luminescence. Vacuum jigs including ultraviolet light sensors are also described.

20 Claims, 5 Drawing Sheets

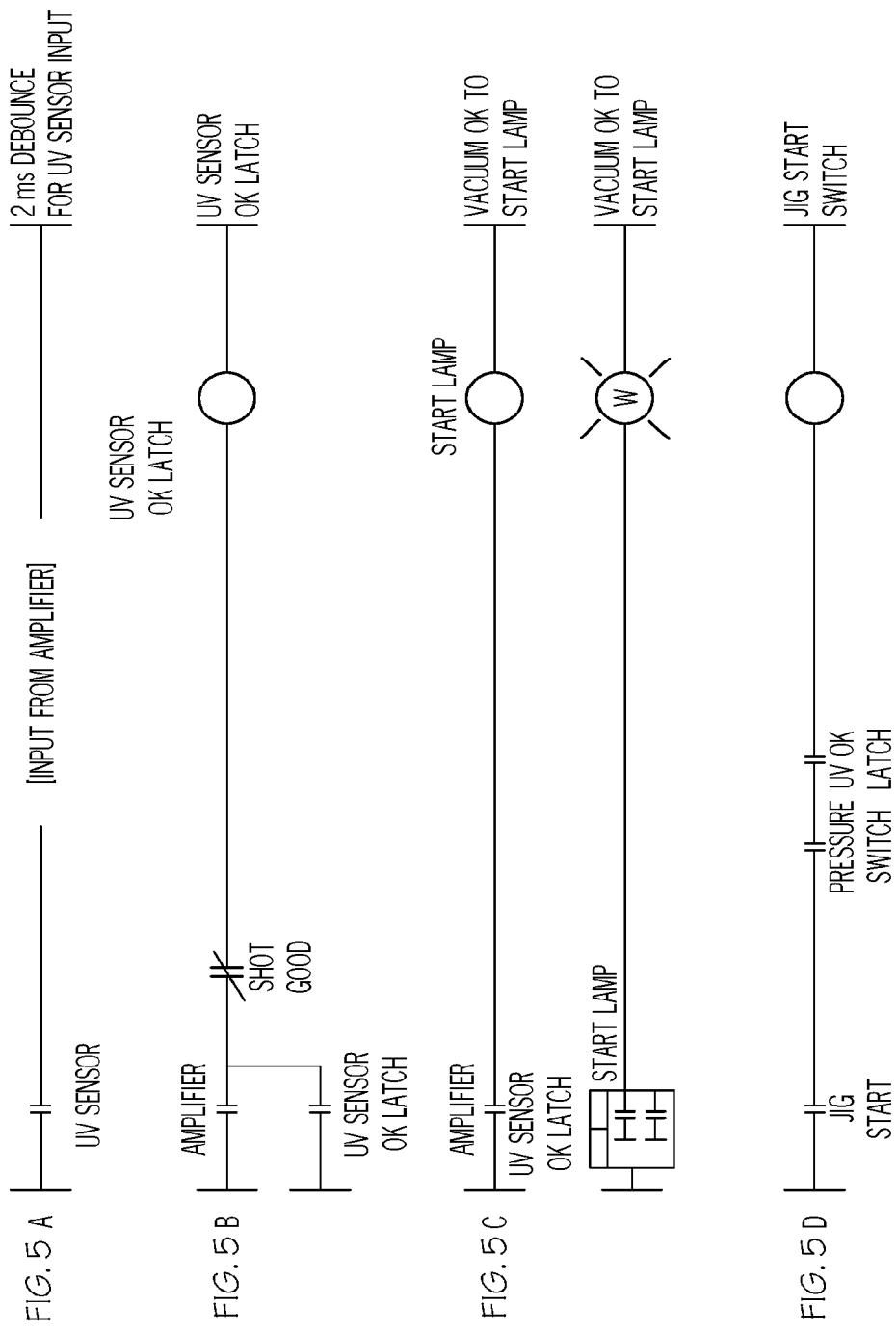

VACUUM JIGS INCLUDING ULTRAVIOLET LIGHT SENSORS AND METHODS OF OPERATING THE SAME

TECHNICAL FIELD

The present specification generally relates to vacuum jigs and, more specifically, to vacuum jigs with ultraviolet light sensors for detecting the presence of an adhesion promoter primer and methods for operating the same.

BACKGROUND

Vacuum jigs may be used in a variety of manufacturing applications, such as to press and hold pieces to be adhered to one another in place while an adhesive is partially or fully cured. For example, vacuum jigs may be used in vehicle manufacturing to press a retainer or sensor clip for receiving a sensor, such as a sonar sensor, onto a vehicle part, such as a bumper. In such applications, an adhesive may be applied to the retainer, while the vehicle part is coated with an adhesion promoter primer.

However, it may be difficult for technicians to determine whether the adhesion promoter primer has been applied to the vehicle part because the adhesion promoter primer may dry transparent. Accordingly, the technician may engage the vacuum jig to pressed the retainer onto a vehicle part that has not been coated with the adhesion promoter primer, resulting in poor adhesion, which may in turn, result in the sensor and retainer falling off after production.

Accordingly, a need exists for alternative vacuum jigs and methods for operating the same to determine the presence of an adhesion promoter primer.

SUMMARY

In one embodiment, a method for operating a vacuum jig may include emitting an ultraviolet light from an ultraviolet light source; detecting, using an ultraviolet light sensor, luminescence of a coating on a surface responsive to emission of the ultraviolet light; determining whether the detected luminescence is greater than or equal to a predetermined threshold luminescence; and enabling a vacuum-assisted coupling of the vacuum jig when the detected luminescence is greater than or equal to the predetermined threshold luminescence.

In another embodiment, a vacuum jig may include an ultraviolet light sensor that includes an ultraviolet light source and a photodetector, a vacuum-assisted coupling for securing the vacuum jig to a surface, and a controller communicatively coupled to the ultraviolet light sensor and the vacuum-assisted coupling. The ultraviolet light sensor is configured to detect a presence of a luminescent material on the surface. The controller includes a processor and a non-transitory memory storing computer readable and executable instructions which, when executed by the processor, cause the vacuum jig to emit ultraviolet light onto the surface with the ultraviolet light source; detect, with the photodetector, luminescence of a coating on the surface responsive to emission of the ultraviolet light; determine, with the controller, whether the detected luminescence is greater than or equal to a predetermined threshold luminescence; and enable the vacuum-assisted coupling when the detected luminescence is greater than or equal to the predetermined threshold luminescence.

In yet another embodiment, a vacuum jig includes a frame, a handle coupled to a first side of the frame to enable a user to hold on to and direct the vacuum jig, a press coupled to a second side of the frame opposing the first side of the frame and configured to move a press head toward and away from the surface, and one or more suction pads for securing the vacuum jig to the surface. Each of the one or more suction pads is coupled to the second side of the frame via a corresponding shaft. The vacuum jig also includes a vacuum pump coupled to the one or more suction pads and configured to draw air through the one or more suction pads to create a vacuum at the one or more suction pads, an ultraviolet light sensor configured to emit an ultraviolet light and detect luminescence of a coating on the surface in response to the ultraviolet light, and a controller communicatively coupled to the ultraviolet light sensor and the vacuum pump. The controller includes a processor and a non-transitory memory storing computer readable and executable instructions which, when executed by the processor, enable the vacuum pump responsive to detection of the luminescence of the coating by the ultraviolet light sensor.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 5A depicts a ladder logic diagram for a controller configured to operate a vacuum jig according to one or more embodiments shown and described herein;

FIG. 5B depicts another ladder logic diagram for a controller configured to operate a vacuum jig according to one or more embodiments shown and described herein;

FIG. 5C depicts another ladder logic diagram for a controller configured to operate a vacuum jig according to one or more embodiments shown and described herein; and FIG. 5D depicts another ladder logic diagram for a controller configured to operate a vacuum jig according to one or more embodiments shown and described herein.

DETAILED DESCRIPTION

Figure 1A:
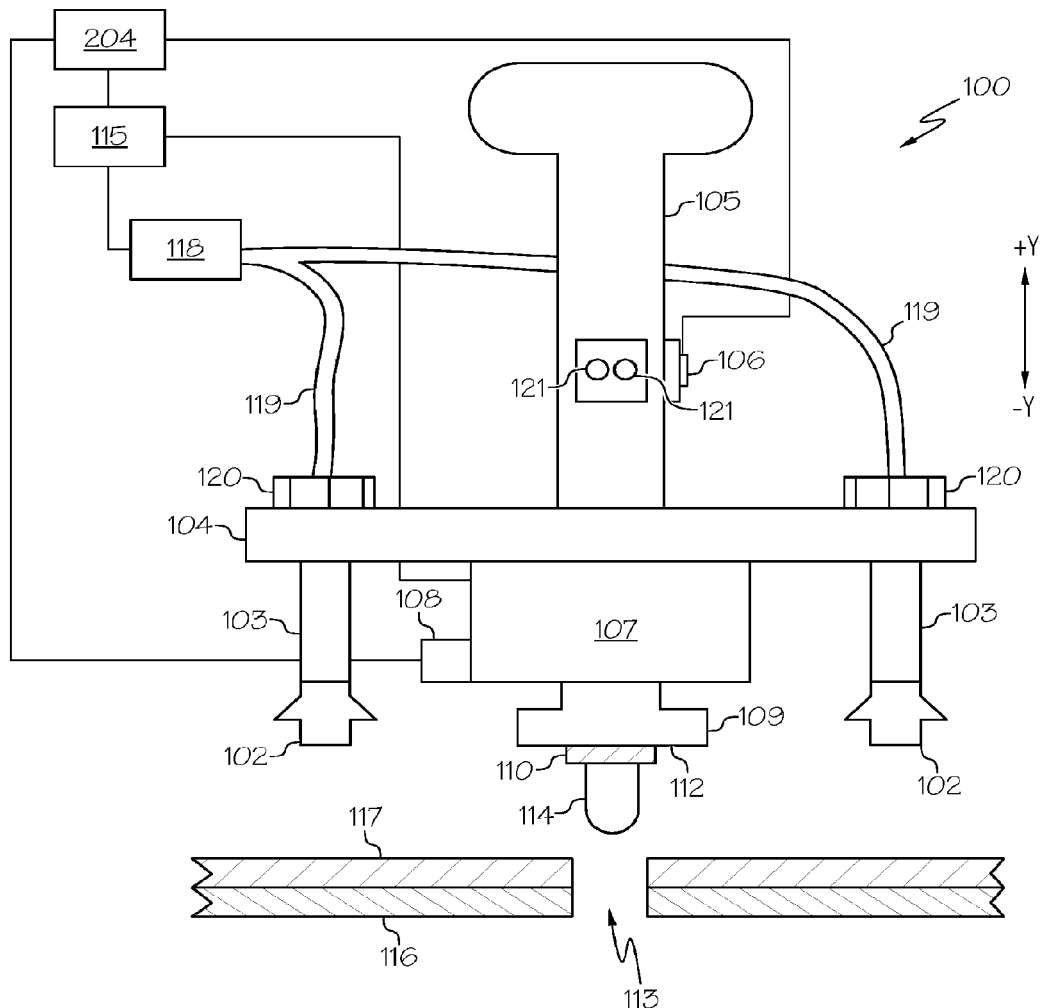
FIG. 1A depicts a vacuum jig including an ultraviolet light sensor according to one or more embodiments shown and described herein.

FIG. 1A generally depicts one embodiment of a vacuum jig for pressing a retainer onto a part responsive to confirming the presence of a coating on the part. For example, the vacuum jig may be used to press a retainer for a sonar sensor onto a bumper of a vehicle responsive to detecting the presence of an adhesion promoter primer. The vacuum jig generally comprises an ultraviolet (UV) light sensor, a vacuum-assisted coupling, and a controller coupled to the UV light sensor and the vacuum-assisted coupling. The controller is configured to enable the vacuum-assisted coupling responsive to a signal from the UV light sensor indicative of the presence of the coating on the part. In embodiments, because the vacuum-assisted coupling is enabled responsive to the signal from the UV light sensor indicative of the presence of the coating on the part, installation of retainers onto uncoated parts may be prevented, thus increasing quality control and reducing post-production failures. Various embodiments of the vacuum jig and the operation of the vacuum jig will be described in more detail herein.

Referring now to FIG. 1A, a vacuum jig 100 includes a pair of suction pads 102 for securing the vacuum jig 100 to a surface 116. The suction pads 102 are coupled to a first side of a frame 104 through a pair of shafts 103. In embodiments, more or fewer suctions pads 102 (and associated shafts 103 for coupling the suction pads 102 to the frame 104) may be employed. For example, the vacuum jig 100 may include two, three, or even four or more suction pads 102, depending on the size and shape of the vacuum jig 100. As another example, an embodiment may include only a single suction pad 102 for securing the vacuum jig 100 to the surface 116. However, in various embodiments, at least two suction pads 102 are employed to provide stability to the vacuum jig 100 when it is secured to the surface 116.

A handle 105 is connected to the frame 104 on a second side of the frame 104 opposing the first side of the frame 104 to enable a user to hold on to and direct the vacuum jig 100. In FIG. 1A, a start button 106 is depicted on the handle 105 to receive input from a user indicating that the vacuum jig 100 is to be started. In embodiments, the start button 106 may be located in other positions, such as on the frame 104 or at a location remote from the vacuum jig 100.

Still referring to FIG. 1A, the vacuum jig 100 may further include a press 107 connected to the frame 104. The press 107, in various embodiments, includes a pneumatic cylinder that is configured to move a press head 109 vertically (e.g., in the +/−Y direction on the axis shown in FIG. 1A) with respect to the frame 104. In other embodiments, the press 107 may include, for example, a hydraulic press or a mechanical press.

The press head 109 includes a press surface 112 and a guide 114. In various embodiments, a part, such as a retainer 110 for a sensor, is slid onto the guide 114, which ensures that the retainer 110 is properly aligned within a space 113 defined within the surface 116. For example, the retainer 110 may be annular in shape and slide around the cylindrically-shaped guide 114. As the press 107 moves the press head in a downward (−Y in FIG. 1A) direction toward the surface 116, the guide 114 may slide through a circular space 113 defined within the surface 116, guiding the retainer 110 into position within or around the space 113. While specific geometries of the retainer 110 and guide 114 have been described, it should be understood that the retainer 110 and guide 114 may have other geometries, depending on the particular embodiment.

Although various embodiments described herein refer to the use of a retainer 110, it is contemplated that in other embodiments, a sensor or other part may be adhered to the surface 116 with an adhesive and the coating 117 without the use of a retainer 110 or other clip. It should be understood that although specific reference is made to a retainer, the vacuum jig 100 may be used to apply other pieces and parts to a surface 116 and a retainer is a non-limiting example of one such piece.

Moreover, although the surface 116 in FIG. 1A is depicted as having a space 113 configured to receive the retainer 110 and/or the sensor retained by the retainer 110, in other embodiments, the surface 116 may include other features for receiving the retainer 110. For example, in some embodiments, the surface 116 may include a recess or lip against which the retainer 110 may be pressed. Alternatively, the retainer 110 may be pressed against the surface 116 (through the coating 117). Embodiments including a space 113 or recess on the surface 116 may enable the retainer 110 and/or the sensor retained by the retainer 110 to be flush with the surface 116. However, in various embodiments, the surface 116 includes at least one surface to which the retainer 110 may be adhered through the adhesive present on the retainer 110 and the coating 117.

The press 107 is connected to an air supply 115 which provides compressed air to the press 107 to vertically drive the press head 109. In various embodiments, the air supply 115 is also connected to a vacuum pump 118, which pulls a vacuum through the suction pads 102 via tubes 119. Although the embodiment depicted in FIG. 1A employs a single air supply 115 to supply air to the press 107 and the vacuum pump 118, in other embodiments, separate air supplies may be used for each of the press 107 and the vacuum pump 118. In still other embodiments, such as embodiments in which the press 107 is a hydraulic press or mechanical press and the vacuum is configured to operate without an air supply, the vacuum jig 100 may not include an air supply 115.

In embodiments, the air supply 115 may include at least one air valve and a solenoid (not shown). In such embodiments, when the air supply 115 is activated, such as will be described in greater detail below, the air valve may be opened to enable the air supply 115 to take in air from the environment, which is compressed and provided to the press 107 and/or vacuum pump 118. In other embodiments, the air supply 115 may include other mechanisms which enable the air supply 115 to supply compressed air to other components of the vacuum jig 100.

In the embodiment depicted in FIG. 1A, the tubes 119 are coupled to the frame 104 via hex nuts 120. It is contemplated that other types of nuts, bolts, or couplers may be employed to couple the tubes 119 to the frame 104 and, thus, the suction pads 102. Furthermore, it should be understood that the tubes 119 are received by couplings in the frame 104 that enable air drawn through the suction pads 102 and corresponding shafts 103 to pass through the frame 104 and through the tubes 119 to the vacuum pump 118. For example, the frame 104 may include a through-bore that enables the tubes 119 to be coupled with the shafts 103.

In the embodiment depicted in FIG. 1A, the vacuum pump 118 is a Venturi vacuum pump. Accordingly, when the air supply 115 provides a flow of compressed air to the vacuum pump 118, the vacuum pump draws air through the suction pads 102, the shafts 103, and the tubes 119 toward the vacuum pump 118, thus creating a vacuum at the suction pads 102 as air is drawn into the system.

In other embodiments, other types of vacuum pumps may be employed. For example, in some embodiments, the vacuum pump 118 may be a mechanical vacuum pump. In such embodiments, the vacuum pump 118 may include at least one air valve such that opening the air valve enables the vacuum pump 118 to draw an air flow through the system (e.g., through the suction pads 102, shafts 103, and tubes 119) in the form of a vacuum. In such embodiments, the air supply 115 may not be coupled to the vacuum pump 118. In various embodiments, at least the vacuum pump 118, the suction pads 102, the components located between the vacuum pump 118 and the suction pads 102 form a vacuum-assisted coupling operable to couple the vacuum jig 100 to the surface 116.

Still referring to FIG. 1A, a UV light sensor 108 is positioned along a side of the press 107. It is contemplated that the UV light sensor 108 may be located elsewhere on the vacuum jig 100, provided it is able to detect luminescence produced by a coating 117 on the surface 116 to which the vacuum jig 100 is to be secured, as will be described hereinbelow. For example, the UV light sensor 108 may be located on the frame 104, along one of the shafts 103, on a side of the press head 109, or elsewhere such that the UV light sensor 108 has an unobstructed view of the surface 116 and the coating 117 thereon. In various embodiments, the UV light sensor 108 detects luminescence resulting from the presence of a coating 117, such as an adhesion promoter primer, on the surface 116. The adhesion promoter primer may be any suitable adhesion promoter primer known and used in the industry, provided that the adhesion promoter primer exhibits luminescence when exposed to UV light. In embodiments, the adhesion promoter primer is applied to the surface 116 of a part, such as the surface of a bumper of a vehicle, and helps bond the retainer 110 to the surface 116. In particular, the adhesion promoter primer may enhance the bond between the adhesive applied to the retainer 110 and the surface 116.

Figure 1B:
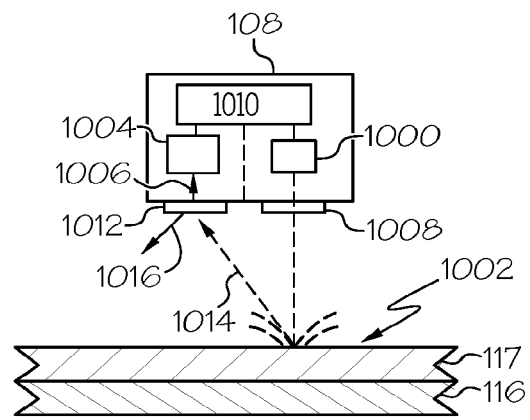
FIG. 1B depicts the ultraviolet light sensor of FIG. 1A in greater detail according to one or more embodiments shown and described herein.

Referring now to FIG. 1B, the UV light sensor 108 is depicted in greater detail. In various embodiments, such as the embodiment depicted in FIG. 1B, the UV light sensor 108 is a luminescence sensor which emits UV light and detects the resulting visible glow caused by the interaction of the UV light with a phosphorescent material, such as the coating 117. In embodiments, the UV light sensor 108 may emit UV light at one or more wavelengths from about 350 nm to about 380 nm. Accordingly, in various embodiments, the UV light sensor 108 includes a UV light source 1000, which emits UV light 1002, a photodetector 1004 (such as a photo diode or the like) that detects visible light 1006 emitted by the target (e.g., the coating 117) when the UV light 1002 strikes the target, and a lens 1008 that directs the UV light 1002 toward the target (e.g., the coating 117). The UV light sensor 108 further includes an electronic circuit 1010 that provides power to the UV light source 1000 and photodetector 1004 and produces an output. In embodiments, the UV light sensor 108 further includes a dichroic mirror 1012 that separates the reflected light 1014 into UV light 1016, which is directed away from the photodetector 1004, and visible light 1006, which is directed toward the photodetector 1004.

Returning to FIG. 1A, the UV light sensor 108, along with at least the air supply 115 and/or the vacuum pump 118 and the start button 106, are connected to a controller 204. The controller 204, as will be described in greater detail hereinbelow, is configured to enable the vacuum-assist coupling by initiating a vacuum responsive to the detection of a luminescent material on the surface 116, such as the coating 117.

In some embodiments, the controller 204 is configured to enable the vacuum pump 118, through the air supply 115, responsive to receiving user input via the start button 106 and an output from the UV light sensor 108, such as the output from the electronic circuit 1010 of the UV light sensor 108. As a non-limiting example, responsive to the detection of the coating 117, the controller 204 may activate the air supply 115 (and thus enable the vacuum-assisted coupling) by sending a signal to the solenoid of the air supply 115 to pull back, which opens the air valve to enable the air supply 115 to draw in air. The air is then compressed and provided to the press 107 and/or the vacuum pump 118. In other embodiments, responsive to the detection of the coating 117, the controller 204 may activate the air supply 115 in other ways, depending on the particular embodiment and air supply 115 included therein.

In still other embodiments, the controller 204 may enable the vacuum-assist coupling through activation of the vacuum pump 118 rather than the air supply 115. In such embodiments, the air supply 115 may be activated independent of detection of a luminescent material (e.g., the air supply 115 may be activated when the user presses the start button 106) and, responsive to the detection of the coating 117, the controller 204 may open or close one or more valves associated with the vacuum pump 118 to enable the vacuum to be drawn through the system. In other words, the air supply 115 may be activated when the user presses the start button 106, but the vacuum pump 118 may be disabled such that a vacuum is not drawn through the system until the vacuum pump 118 is enabled by the controller 204 responsive to the detection of the coating 117. Regardless of the specific location at which the controller 204 operates control over the vacuum-assisted coupling to enable or disable the vacuum-assisted coupling, in various embodiments, the vacuum-assisted coupling cannot be enabled without the detection of the luminescent material (e.g., the coating 117) on the surface 116.

In the embodiment depicted in FIG. 1A, the vacuum jig 100 also includes one or more indicators 121 coupled to the controller 204. The indicators 121 may be used, for example, to indicate that the vacuum pump 118 is being activated or is prevented from being activated, or that a luminescence signal has or has not been received from the UV light sensor 108. In other embodiments, the indicators 121 may simply indicate that the vacuum jig 100 is ready for use or has detected one or more errors. In some embodiments, the indicators 121 may be lights, for example white lights, colored lights, or a combination thereof, or another type of visual indication. In other embodiments, the indicators 121 may be speakers configured to emit an audible signal. In still other embodiments, the indicators 121 may be tactile elements configured to provide a tactile indication. In other embodiments, the indicators 121 may include at least two of a visual indicator, an auditory indicator, and a tactile indicator. In various embodiments, the indicators 121 are activated by the controller 204 to indicate a status of the vacuum jig 100. In FIG. 1A, the indicators 121 are shown as being positioned on the handle 105, although in other embodiments, the indicators 121 may be positioned elsewhere on the vacuum jig 100, such as on the frame 104, or remote from the vacuum jig 100. However, it should be understood that the indicators 121 are optional.

In operation, a part (e.g., a retainer 110 for a sonar sensor) is placed around the guide 114 and against the press surface 112 of the press head 109 in preparation for adhesion to a surface 116. The retainer 110 may have an adhesive on a surface of the retainer 110 opposite the surface of the retainer 110 in contact with the press surface 112. The adhesive may be applied to the retainer 110 before or after the retainer 110 is positioned against the press surface 112. Using the handle 105, a user guides the vacuum jig 100 over the surface 116 and places the suction pads 102 in contact with a coating 117 on the surface 116 to which the retainer 110 is to be adhered. The start button 106 receives a user input to begin operation of the vacuum jig 100. In embodiments, when a user pushes the start button 106, the start button 106 transmits a signal to the controller 204, which is electrically coupled to the start button 106, the air supply 115, and the UV light sensor 108. As will be described in greater detail hereinbelow, in various embodiments, the air supply 115 is not turned on by the controller 204 until the receipt of a signal indicative of luminescence of the coating 117 from the UV light sensor 108.

When the air supply 115 is activated by the controller 204, it provides compressed air to the vacuum pump 118 which draws air through the suction pads 102 to provide a suction force, which draws the vacuum jig 100 down (in the −Y direction in FIG. 1A) toward the surface 116. In addition to providing compressed air to the vacuum pump 118, the air supply 115 further provides compressed air to the press 107 which drives the press head 109, the guide 114, and the retainer 110 positioned around the guide 114 down toward the surface 116. In such embodiments, a pressing force on the retainer 110, transferred to the retainer 110 through the press head 109 of the press 107, presses the retainer 110 onto the coating 117 and holds the retainer 110 in place while the adhesive is cured. In embodiments, the adhesive may be fully or partially cured while the retainer 110 is being pressed.

After a predetermined amount of time has passed, the air supply 115 is turned off, which in turn causes the press 107 to move the press head 109 away from the surface 116 and the retainer 110, and causes the vacuum drawn through the suction pads 102 by vacuum pump 118 to decrease until the vacuum-assisted coupling may be released from the surface 116. The user may use the handle 105 to raise the vacuum jig 100 away from the surface 116. Then, a new retainer 110 may be placed on the guide 114 and the process may be repeated.

Figure 2:
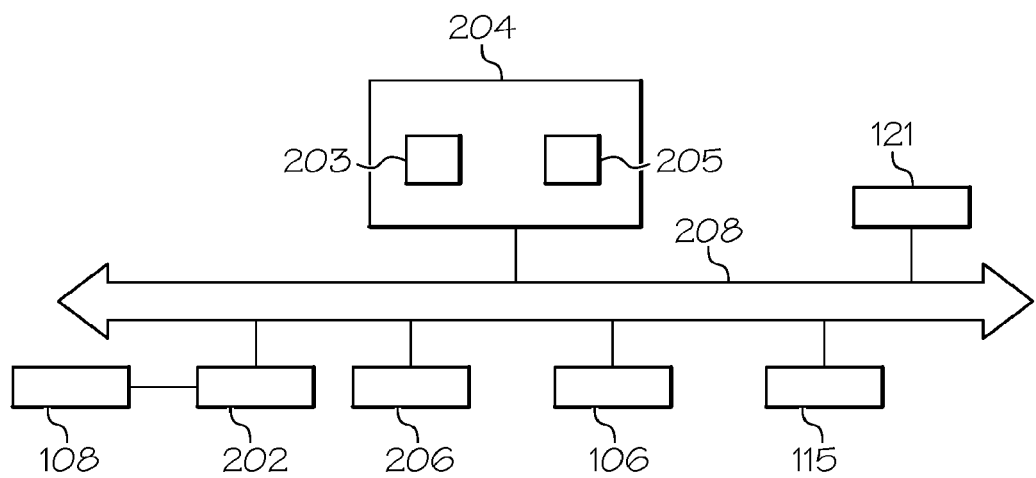
FIG. 2 depicts a block diagram of a system for operating a vacuum jig according to one or more embodiments shown and described herein.

Referring now to FIG. 2, a control system 200 for the vacuum jig 100 is schematically depicted. The control system 200 includes the controller 204 communicatively coupled to the UV light sensor 108, an amplifier 202, and a pressure sensor 206 through a communication pathway 208. The controller 204 is also communicatively coupled to the start button 106 to receive a user input indicative that the vacuum jig 100 should be operated, the air supply 115, and the indicators 121, as described herein, through the communication pathway 208. As used herein, the term "communicatively coupled" means that coupled components are capable of exchanging data signals with one another such as, for example, electrical signals via a conductive medium, electromagnetic signals via air, optical signals via optical waveguides, and the like.

In various embodiments, the controller 204 is a programmable logic controller (PLC). The PLC may comprise one or more processors 203 capable of executing machine readable instructions stored in a memory component 205, such as an integrated circuit, a microchip, a computer, or any other computing device. The memory component 205 may be configured as a volatile and/or nonvolatile non-transitory computer readable medium and, as such, may include random access memory (including SRAM, DRAM, and/or other types of random access memory), flash memory, registers, compact discs (CD), digital versatile discs (DVD), magnetic disks, and/or other types of storage components. Additionally, the memory component 205 may be configured to store, among other things, operation logic as described in more detail below. The memory component 205 may also store data, such as data captured by the UV light sensor 108 or externally acquired data, for determining whether the vacuum-assisted coupling should be enabled, as will be described.

In embodiments, the communication pathway 208 may provide signal interconnectivity between various components of the control system 200. Accordingly, the communication pathway 208 may be formed from any medium that is capable of transmitting a signal such as, for example, conductive wires, conductive traces, optical waveguides, or the like. Although not depicted in FIG. 2, the control system 200 may also include one or more network interface modules, to connect the vacuum jig 100 to a remote computing device or a remote computer network. The network interface module may include any wired or wireless networking hardware, such as a modem, LAN port, wireless fidelity (Wi-Fi) card, WiMax card, mobile communications hardware, and/or other hardware for communicating with other networks and/or devices, such as other devices on a manufacturing line in which the vacuum jig 100 may be employed. Thus, in some embodiments, the communication pathway 208 may facilitate the transmission of wireless signals, such as WiFi, Bluetooth, and the like.

In embodiments, the memory component 205 of the controller 204 is a non-transitory memory component that stores computer readable and executable instructions which, when executed by the processor 203, cause the UV light sensor 108 to emit UV light onto the surface 116, receive a luminescence signal from the photodetector 1004 of the UV light sensor 108 corresponding to an amount of visible light produced by the luminescent material (e.g., the coating 117), and enable the vacuum-assisted coupling responsive to determining that the received luminescence signal exceeds a predetermined threshold luminescence.

In various embodiments, the UV light sensor 108 provides the output (sometimes referred to herein as a luminescence signal) corresponding to the intensity of the luminescence (or an amount of visible light produced by the coating 117) to the amplifier 202. The amplifier 202 interprets the output of the UV light sensor 108 and assigns a digital value to the UV light sensor output. In some embodiments, the assigned digital value corresponds to an amplified luminescence signal, which ranges from 0 to 9,999 where 0 corresponds to 0% UV light reflected and 9,999 corresponds to 100% UV light reflected. In embodiments, the amplified luminescence signal is from about 2,000 to about 5,000, from about 2,500 to about 4,500, or from about 3,000 to about 4,000 when the coating 117 is present on the surface 116. However, it should be noted that in other embodiments, the amplifier 202 may employ a different scale, or may not be used to amplify the output of the UV light sensor 108 at all.

In embodiments, the amplifier 202 transmits the amplified luminescence signal to the controller 204. Although referred to herein as an "amplified luminescence signal," it should be understood that in various embodiments, a value representing an intensity of the signal, and not the signal itself, is transmitted. Thus, as used herein, the term "signal" includes values representative of the intensity of the signal and other derivatives of the signal. In some embodiments, the amplifier 202 may compare the amplified luminescence signal to a predetermined threshold luminescence stored in a memory component of the amplifier 202 (not shown) and, responsive to determining that the amplified luminescence signal is greater than or equal to the predetermined threshold luminescence, provide an output to the controller 204 indicative that luminescence has been detected. The output may be, for example, the value corresponding to the amplified luminescence signal or an indication that the amplified luminescence signal is greater than or equal to the predetermined threshold luminescence.

In other embodiments, instead of the amplifier 202 comparing the amplified luminescence signal to a predetermined threshold luminescence, the amplifier 202 may amplify the output of the UV light sensor 108 and provide the amplified luminescence signal to the controller 204, which compares the amplified luminescence signal to a predetermined threshold luminescence stored in the memory component 205 to determine whether the vacuum-assisted coupling should be enabled.

As shown in FIG. 2, the controller 204 is further connected to a pressure sensor 206. The pressure sensor 206 is configured to measure the pressure of the vacuum force at the suction pads 102 and provide feedback to the controller 204. Based on the feedback of the pressure sensor 206, the controller 204 may adjust the operation of the vacuum-assisted coupling. For example, if the pressure sensor 206 measures a pressure that is less than a predetermined pressure setting stored in the memory component 205, the controller 204 may decrease the vacuum pulled by the vacuum pump 118. Alternatively, if the pressure sensor 206 measures a pressure that is greater than a predetermined pressure setting, the controller 204 may increase the vacuum pulled by the vacuum pump 118. The amount of vacuum pulled by the vacuum pump 118 may be adjusted, for example, by adjusting the amount of air supplied by the air supply 115, or by another method, depending on the particular embodiment and type of vacuum pump 118 employed. In embodiments, the predetermined pressure setting may be a range of acceptable pressures. For example, the predetermined pressure setting may be from about −70 kPa to about −80 kPa. It should be understood that the predetermined pressure setting may vary depending on the particular embodiment. Moreover, in some embodiments, a pressure sensor 206 may not be included.

Still referring to FIG. 2, the controller 204 is communicatively coupled to the optional indicators 121 through the communication pathway 208. As will be described in greater detail in conjunction with FIG. 5C, the controller 204 is configured to turn on or off the indicators 121 depending on inputs received from other components of the control system 200, including, but not limited to, the amplifier 202 and the start button 106.

Figure 3:
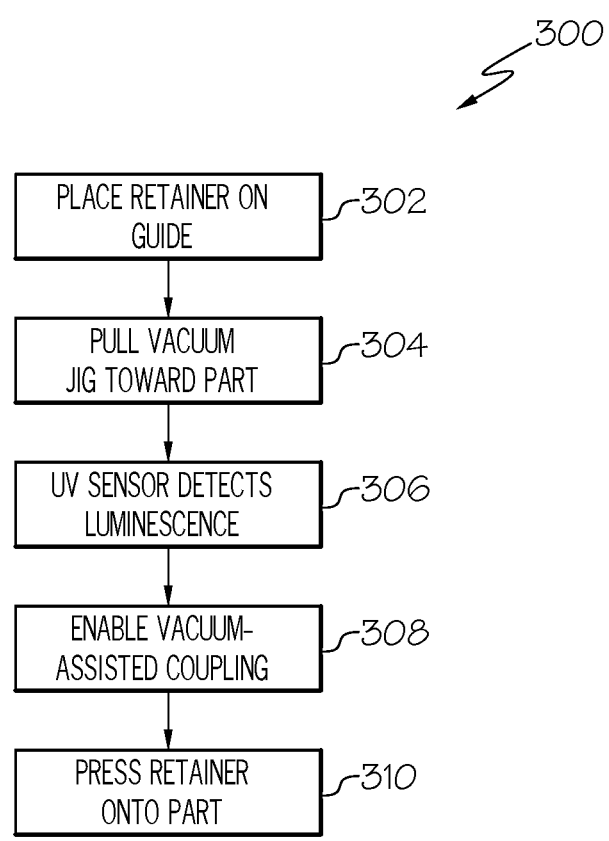
FIG. 3 is a flow diagram of a method for installing a sensor retainer onto part using a vacuum jig according to one or more embodiments shown and described herein.

In operation, the vacuum jig 100 may be used to adhere a retainer 110 to a coating 117 on a surface 116. The retainer 110 may be employed to couple a sensor, such as a sonar sensor or other type of sensor, to a vehicle part, such as a bumper. FIG. 3 is a flow diagram of an example method of attaching a retainer 110 onto a surface 116 using the vacuum jig 100. At step 302, the retainer 110 is placed around the guide 114 and against the press surface 112. In embodiments, an adhesive is applied to a surface of the retainer 110 proximate the surface 116 such that when the retainer 110 is pressed against the coating 117 on the surface 116, the adhesive on the surface of the retainer 110 and the coating 117 form an adhesive bond. Next, at step 304, the vacuum jig 100 is pulled toward the part (e.g., the bumper). In particular, the suction pads 102 may be placed in contact with the coating 117 on the surface 116 by a user directing the vacuum jig 100 using the handle 105.

Then, at step 306, the UV light sensor 108 detects luminescence produced by the coating 117. In embodiments, the UV light sensor 108 emits UV light with the UV light source 1000 onto the coating 117, which illuminates, and detects the luminescence with the photodetector 1004. The electronic circuit 1010 of UV light sensor 108 provides an output corresponding to the intensity of the luminescence, which is transmitted to the controller 204.

As described hereinabove, in some embodiments, the UV light sensor 108 may provide an output to the amplifier 202, which digitizes and amplifies the signal and compares the amplified luminescence signal to a predetermined threshold luminescence. When the amplified luminescence signal exceeds or is equal to the predetermined threshold luminescence, the amplifier 202 provides an output to the controller 204. However, in other embodiments, the UV light sensor 108 may provide the output directly to the controller 204 for comparison to the predetermined threshold luminescence.

At step 308, the vacuum-assisted coupling is enabled. In one embodiment, at step 308, the air supply 115 is enabled by the controller 204 and provides compressed air to the vacuum pump 118, which in turn operates to draw a vacuum through the suction pads 102, pulling the suction pads 102 and the frame 104 toward the surface 116. However, as described above and below, in various embodiments, the controller 204 may enable the vacuum-assisted coupling in other ways, such as by operating valves or otherwise activating the vacuum pump 118.

At step 310, when powered on, the air supply 115 further provides compressed air to the press 107, which drives the press head 109 down (in the −Y direction in FIG. 1A) toward the surface 116, pressing the retainer 110 onto the coating 117 on the surface 116 of the part (e.g., the bumper).

Figure 4:
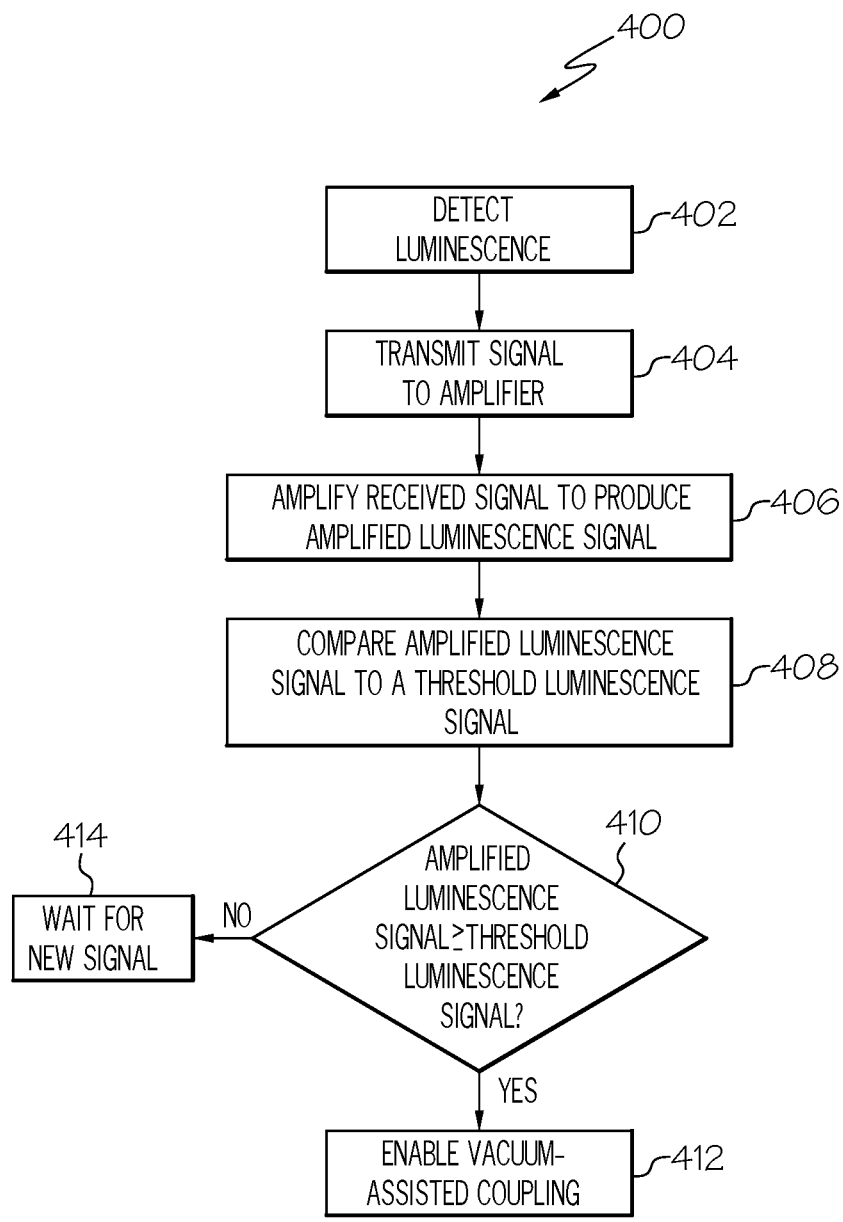
FIG. 4 is a flow diagram of a method for enabling a vacuum-assisted coupling of a vacuum jig responsive to detecting luminescence according to one or more embodiments shown and described herein.

As described above and below, in some embodiments, a predetermined threshold luminescence is used to determine whether the coating 117 is present on the surface 116. An example method 400 for using the predetermined threshold luminescence is depicted in FIG. 4. In step 402, the UV light sensor 108 detects luminescence of the coating 117 with the photodetector 1004, as in step 306 of method 300, which results from exposure of the coating 117 to UV light 1002 emitted by the UV light source 1000 of the UV light sensor 108. The UV light sensor 108 transmits a signal, using the electronic circuit 1010, for example, that corresponds to the detected luminescence to the amplifier 202 in step 404.

Next, at step 406, the amplifier 202 amplifies the received signal to produce an amplified luminescence signal. In step 408, the amplifier 202 compares the amplified luminescence signal to a threshold luminescence signal (i.e., the predetermined threshold luminescence) stored in a memory of the amplifier 202. At step 410, the amplifier 202 determines whether the amplified luminescence signal is greater than or equal to the threshold luminescence signal. If the amplified luminescence signal is greater than or equal to the threshold luminescence signal (e.g., a "yes" at step 410), the vacuum-assisted coupling is enabled at block 412. For example, the amplifier 202 may transmit a signal to the controller 204 which enables the vacuum-assisted coupling, as described above and below.

However, if the amplified luminescence signal is less than the threshold luminescence signal (e.g., a "no" at step 410), the amplifier 202 waits for a new signal from the UV light sensor 108. For example, when the adhesion promoter primer (i.e., the coating 117) is not present on the surface 116, the amplified luminescence signal may be less than the threshold luminescence signal, or may even be 0. Accordingly, when the coating 117 is not present on the surface 116, the UV light sensor 108 does not detect the desired level of luminescence and the vacuum-assisted coupling is not enabled.

Although in method 400 the amplifier 202 is described as performing the comparison between the amplified luminescence signal and the threshold luminescence signal, it is also contemplated that the controller 204 may perform the comparison. In such embodiments, the amplifier 202 may transmit the amplified luminescence signal to the controller 204, which compares the amplified luminescence signal to the threshold luminescence signal stored in the memory component 205.

In still other embodiments, such as embodiments that do not include an amplifier 202, the UV light sensor 108 may transmit the luminescence signal to the controller 204, which may compare the luminescence signal to a predetermined threshold luminescence stored in the memory component 205.

In various embodiments, the controller 204 enables the vacuum-assisted coupling after confirming the presence of the adhesion promoter primer, as indicated by a luminescence signal produced by the UV light sensor 108. More specifically, the controller 204 is configured to execute, on one or more processors 203, computer-readable instructions that enable the vacuum-assisted coupling. FIGS. 5A-5D depicts various ladder logic diagrams for use in accordance with various embodiments. In particular, the ladder logic diagrams depicted in FIGS. 5A-5D illustrate various inputs and outputs of the controller 204 and are representative of the computer-readable instructions stored in the memory component 205 and executed by the controller 204 on the processor 203.

As shown in FIG. 5A, the controller 204 is programmed to establish a debounced input for the UV light sensor 108. In particular, once the UV light sensor 108 is actuated, the controller 204 waits for input from the amplifier 202 and ensures that only one input received from the amplifier 202 is registered by the controller 204 over a time period of 2 ms, for example. Other inputs may, for example, be ignored. In some embodiments, the UV light sensor 108 is configured to obtain a reading once every 2 ms upon activation by a user, such as when the user presses the start button 106.

FIG. 5B depicts a ladder logic diagram which establishes a latch for UV light sensor input. In particular, when the amplifier 202 transmits a signal, and if the vacuum jig 100 has not already engaged (e.g., the vacuum-assisted coupling is not already coupled to a surface), the UV light sensor OK latch is energized. The UV light sensor OK latch remains energized until it is reset by the ending of vacuum (e.g., the vacuum pump 118 and/or the air supply 115 is turned off).

In FIG. 5C, the ladder logic diagram shows that, optionally, when the UV light sensor OK latch is energized, the controller 204 energizes a lamp. The lamp may be, for example, one of the indicators 121 shown in FIG. 1A that indicates that the vacuum is starting or is enabled. In some embodiments, such as shown in the second ladder logic diagram of FIG. 5C, actuating the "vacuum okay to start lamp" (which may be, for example a colored indicator light), may also cause a white lamp to be energized.

FIG. 5D depicts a ladder logic diagram for starting the vacuum jig 100. As shown in FIG. 5D, if the jig start button (e.g., the start button 106) is actuated, the pressure switch is actuated, and the UV light sensor OK latch is actuated, the jig start switch is energized and the press 107 is actuated. In various embodiments, the pressure switch is actuated after the vacuum pump 118 has been actuated and draws a vacuum through the suction pads 102, which enables the vacuum-assisted coupling to secure the vacuum jig 100 to the coating 117 on the surface 116 and maintain a predetermined pressure that is measured by the pressure sensor 206.

In such embodiments, the press 107 is actuated after the vacuum-assisted coupling. It is contemplated that more or fewer inputs may be employed, depending on the particular embodiment. For example, in some embodiments, the vacuum jig 100 may be operated only a predetermined number of times before it needs to be reset and a counter provides a signal to the controller 204. As another example, the controller 204 may receive input from other parts on an assembly line, such as a conveyor system, to determine that a part (e.g., a bumper) is in position before the vacuum jig 100 is operable.

Although FIGS. 5A-5D depict ladder logic diagrams suitable for programming the controller 204 in accordance with various embodiments, it is contemplated that other computer executable instructions may be provided to the controller 204 enable the controller 204 to activate the operation of the vacuum-assisted coupling responsive to detecting luminescence from the coating 117.

In various embodiments described herein, a controller 204 electronically enables the vacuum-assisted coupling responsive to the detection of luminescence of a surface. However, in alternative embodiments, the vacuum-assisted coupling may be enabled through hardware. For example, the UV light sensor 108 may provide an output to a switch positioned between the air supply 115 and the start button 106. Accordingly, when the UV light sensor 108 provides an output to the switch indicative of the presence of the coating 117, the switch may turn on, enabling the vacuum-assisted coupling. The switch may be positioned in other circuit locations to enable other components of the vacuum-assisted coupling to be turned on, depending on the particular embodiment.

Having described various embodiments in which the vacuum-assisted coupling is enabled responsive to detecting the presence of a coating 117 on the surface 116, consider now a contrasting example in which the coating 117 is absent on the surface 116.

In this contrasting example, a retainer 110 is placed around the guide 114 and against the press surface 112 of the press head 109 in preparation for adhesion to a surface 116. The retainer 110 has an adhesive on a surface of the retainer 110 opposite the surface of the retainer 110 in contact with the press surface 112. Using the handle 105, a user guides the vacuum jig 100 over the surface 116 and places the suction pads 102 in contact with the surface 116 to which the retainer 110 is to be adhered. The user pushes the start button 106, which receives the user input to begin operation of the vacuum jig 100. The start button 106 transmits a signal to the controller 204, which is electrically coupled to the start button 106, the air supply 115, and the UV light sensor 108.

The UV light sensor 108, through the UV light source 1000, emits UV light 1002 toward the surface 116. However, instead of providing luminescence, the surface 116 absorbs all or part the UV light 1002. Accordingly, the reflected light 1014 from the surface 116, if any, may include little, if any, visible light 1006. In embodiments in which there is no visible light reflected by the surface 116, the photodetector 1004 does not detect a signal and the UV light sensor 108 does not provide an output. Accordingly, the controller 204 does not receive an output from the UV light sensor 108 (or the amplifier 202), and does not enable the vacuum-assisted coupling. For example, the controller 204 does not enable the air supply 115 to be activated to provide compressed air to the vacuum pump 118 and/or the press 107.

If there is visible light 1006 reflected from the surface 116, such as in embodiments where the surface 116 produces a small amount of luminescence (e.g., less than the luminescence produced by the coating 117), the photodetector 1004 detects the visible light 1006 and, using the electronic circuit 1010, the UV light sensor 108 generates an output corresponding to the luminescence signal. This luminescence signal, in various embodiments, is less than a luminescence signal produced by the UV light sensor 108 when a coating 117 is present on the surface.

In various embodiments, the luminescence signal is transmitted to the amplifier 202, which amplifies the signal and compares the amplified luminescence signal to a threshold luminescence signal stored in a memory of the amplifier 202. Because the amount of visible light, and thus the luminescence signal and the corresponding amplified luminescence signal, are lower than the corresponding values produced by a coating 117, the amplified luminescence signal is not greater than or equal to the threshold luminescence signal. Therefore, in various embodiments, the amplifier 202 does not provide an output to the controller 204, which, in turn, does not enable the vacuum-assisted coupling.

Various embodiments described herein include vacuum jigs having an ultraviolet light sensor for detecting luminescence on a surface resulting from the presence of a coating, such as an adhesion promoter primer. In various embodiments, the vacuum-assisted coupling, which secures the vacuum jig to the surface, is enabled responsive to detection of the luminescence. Accordingly, the vacuum jig is activated when the adhesion promoter primer is present and is disabled in the absence of the adhesion promoter primer, which may improve quality control for sensor retainers adhered to the surface using the vacuum jig.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for operating a vacuum jig comprising:
emitting an ultraviolet light from an ultraviolet light source;
detecting, using an ultraviolet light sensor, luminescence of a coating on a surface responsive to emission of the ultraviolet light;
determining whether the detected luminescence is greater than or equal to a predetermined threshold luminescence; and
enabling a vacuum-assisted coupling of the vacuum jig when the detected luminescence is greater than or equal to the predetermined threshold luminescence.

2. The method of claim 1, wherein the ultraviolet light sensor is mounted on the vacuum jig.

3. The method of claim 1, wherein enabling the vacuum-assisted coupling comprises initiating a vacuum to secure the vacuum jig to the surface.

4. The method of claim 1, wherein enabling the vacuum-assisted coupling comprises enabling an air supply configured to provide compressed air to a vacuum pump.

5. The method of claim 1, further comprising:
amplifying the detected luminescence to produce an amplified luminescence signal; and
comparing the amplified luminescence signal to the predetermined threshold luminescence,
wherein enabling the vacuum-assisted coupling is performed responsive to determining that the amplified luminescence signal is greater than or equal to the predetermined threshold luminescence.

6. The method of claim 1, further comprising:
pressing a retainer configured to receive a sensor onto the coating.

7. The method of claim 6, wherein the surface comprises a surface of a bumper.

8. A vacuum jig comprising:
an ultraviolet light sensor configured to detect a presence of a luminescent material on a surface, the ultraviolet light sensor comprising an ultraviolet light source and a photodetector;
a vacuum-assisted coupling for securing the vacuum jig to the surface; and
a controller communicatively coupled to the ultraviolet light sensor and the vacuum-assisted coupling, the controller comprising a processor and a non-transitory memory storing computer readable and executable instructions which, when executed by the processor, cause the vacuum jig to:
emit ultraviolet light onto the surface with the ultraviolet light source;
detect, with the photodetector, luminescence of a coating on the surface responsive to emission of the ultraviolet light;
determine, with the controller, whether the detected luminescence is greater than or equal to a predetermined threshold luminescence; and
enable the vacuum-assisted coupling of the vacuum jig when the detected luminescence is greater than or equal to the predetermined threshold luminescence.

9. The vacuum jig of claim 8, further comprising:
an amplifier coupled to the ultraviolet light sensor and configured to amplify the detected luminescence and produce an amplified luminescence,
wherein the amplifier is configured to determine whether the amplified luminescence is greater than or equal to the predetermined threshold luminescence.

10. The vacuum jig of claim 8, further comprising:
an amplifier coupled to the ultraviolet light sensor and configured to amplify the detected luminescence and produce an amplified luminescence,
wherein the computer readable and executable instructions, when executed by the processor, cause the vacuum jig to:
determine, with the controller, whether the amplified luminescence is greater than or equal to the predetermined threshold luminescence.

11. The vacuum jig of claim 8, wherein the vacuum-assisted coupling comprises an air supply, and wherein enabling the vacuum-assisted coupling comprises activating the air supply.

12. The vacuum jig of claim 11, wherein the air supply, when enabled:
draws air in;
compresses the air; and
provides the compressed air to a vacuum pump of the vacuum-assisted coupling.

13. The vacuum jig of claim 12, further comprising a press coupled to the air supply, wherein the air supply, when enabled:
provides compressed air to the press which drives a press head coupled to the press toward the surface.

14. The vacuum jig of claim 8, wherein the vacuum-assisted coupling comprises a vacuum pump, and wherein enabling the vacuum-assisted coupling comprises activating the vacuum pump.

15. The vacuum jig of claim 8, further comprising a start button, wherein the start button is disabled until the vacuum-assisted coupling is enabled.

16. A vacuum jig comprising:
a frame;
a handle coupled to a first side of the frame;
a press coupled to a second side of the frame opposing the first side of the frame and configured to move a press head toward and away from a surface;
one or more suction pads for securing the vacuum jig to the surface, each of the one or more suction pads coupled to the second side of the frame via a corresponding shaft;
a vacuum pump coupled to the one or more suction pads and configured to draw air through the one or more suction pads to create a vacuum at the one or more suction pads;
an ultraviolet light sensor configured to emit ultraviolet light and detect luminescence of a coating on the surface in response to the ultraviolet light; and
a controller communicatively coupled to the ultraviolet light sensor and the vacuum pump, the controller comprising a processor and a non-transitory memory storing computer readable and executable instructions which, when executed by the processor, enable the vacuum pump responsive to detection of the luminescence of the coating by the ultraviolet light sensor.

17. The vacuum jig of claim 16, further comprising:
one or more indicators coupled to the controller to indicate that the vacuum pump is being activated.

18. The vacuum jig of claim 16, wherein the press comprises a guide configured to receive a part to be pressed onto the surface.

19. The vacuum jig of claim 16, further comprising:
an air supply configured to provide compressed air to at least one of the vacuum pump and the press.

20. The vacuum jig of claim 16, further comprising:
an amplifier configured to configured to amplify the luminescence signal and produce an amplified luminescence signal, compare the amplified luminescence signal to the predetermined threshold luminescence, and provide an output to the controller when the amplified luminescence signal is greater than or equal to the predetermined threshold luminescence,
wherein the computer readable and executable instructions, when executed by the processor, enable the vacuum pump responsive to the output from the amplifier.

\* \* \* \* \*